•

US008163953B2

(12) United States Patent
Bahr et al.

(10) Patent No.: US 8,163,953 B2
(45) Date of Patent: Apr. 24, 2012

(54) COMPOUNDS FOR LYSOSOMAL MODULATION AND METHODS OF USE

(75) Inventors: Ben A. Bahr, Hampton, CT (US); Dennis Wright, Storrs, CT (US)

(73) Assignee: University of Connecticut, Farmington, CT (US)

(*) Notice: Subject to any disclaimer, the term of this patent is extended or adjusted under 35 U.S.C. 154(b) by 173 days.

(21) Appl. No.: 12/426,644

(22) Filed: Apr. 20, 2009

(65) Prior Publication Data

US 2009/0281178 A1    Nov. 12, 2009

Related U.S. Application Data

(60) Provisional application No. 61/046,294, filed on Apr. 18, 2008.

(51) Int. Cl.
*A61K 31/70*    (2006.01)
*A61K 31/27*    (2006.01)
*C07C 69/88*    (2006.01)
*C07C 271/20*   (2006.01)

(52) U.S. Cl. ............................ 560/72; 514/487; 514/27

(58) Field of Classification Search .................. 514/27, 514/487; 560/72
See application file for complete search history.

(56) References Cited

U.S. PATENT DOCUMENTS

| 5,545,640 | A  | 8/1996  | Beaulieu et al. |
| 6,140,505 | A  | 10/2000 | Kunda et al. |
| 6,458,760 | B1 | 10/2002 | Seyfried et al. |
| 7,119,105 | B2 | 10/2006 | Ellman et al. |
| 2002/0094958 | A1 | 7/2002 | Bahr |
| 2004/0044072 | A1 | 3/2004 | TenBrink et al. |
| 2006/0014737 | A1 | 1/2006 | John et al. |
| 2007/0037868 | A1 | 2/2007 | Marcin et al. |

FOREIGN PATENT DOCUMENTS

| DE | 3829594 | | 3/1990 |
| DE | 4030350 | | 4/1991 |
| WO | WO-9200750 | | 1/1992 |
| WO | WO-9403468 | | 2/1994 |
| WO | WO-0056335 | | 9/2000 |
| WO | WO-0202512 | | 1/2002 |
| WO | WO-02098849 | | 12/2002 |
| WO | WO-2004050609 | | 6/2004 |
| WO | WO 2005062979 | * | 7/2005 |
| WO | WO 2005087714 A2 | * | 9/2005 |
| WO | WO-2009129532 A1 | | 5/2009 |

OTHER PUBLICATIONS

Miller et al. Novel arysulfonamides possessing sub-picomolar HIV protease activities and potent anti-HIV activity against wild-type and drug-esistant viral strains. Bioorganic & Medicinal Chemistry Letters, 2004, 14 (4), pp. 959-963. ISSN: 0960-894X.*
"International Application Serial No. PCT/US2009/041113, Search Report mailed Jul. 23, 2009".
Beaulieu, Pierre L. et al., "Potent HIV Protease Inhibitors Containing a Novel (Hydroxyethyl)amide Isostere", J. Med. Chem 1997, 40, 2164-2176.
Bendiske, Jennifer et al., "Lysosomal Activation is a Compensatory Response Against Protein Accumulation and Associated Synaptopathogenesis—An approach for Slowing Alzheimer Disease?", Journal of Neuropathology and Experimental Neurology May 2003, vol. 62, No. 5, pp. 451-463.
Butler, David et al., "Cellular Responses to Protein Accumulation Involve Autopagy and Lysosomal Enzyme Activation", Rejuvenation Research 2005, vol. 8 No. 4, pp. 227-237.
Butler, D. et al., "Lysosomal enhancement promotes functional recovery in the APPSwind mouse model of Alzheimer's disease", Oasis—Online Abstract Submission and Invitation System Nov. 4, 2007, Program # 157.13/U24.
Butler, David et al., "Potential Compensatory Responses Through Autophagic/Lysosomal Pathways in Neurodegenerative Diseases", Augophagy Sep. 2006, vol. 2, Issue 3, 234-237.
Callahan, Linda M. et al., "Quantitative Decrease in Synaptophysin Message Expression and Increase in Cathepsin D Message Expression in Alzheimer Disease Neurons Containing Neurofibrillary Tangles", Journal of Neuropathology and Experimental Neurology Mar. 1999, vol. 58, No. 3, pp. 275-287.
Coleman, Paul et al., "A focus on the synapse for neuroprotection in Alzheimer disease and other dementias", Neurology 2004, 63:1155-1162.
Cuervo, Ana M. et al., "Autophagy and Aging—The Importance of Maintaining "Clean" Cells", Autophagy 2005, 1:3, 131-140.
Holmes, Duncan S. et al., "Synthesis and Structure—Activity Relatioships of a Series of Penicillin-Derived HIV Proteinase Inhibitors Containing a Stereochemically Unique Peptide Isostere", J. Med. Chem 1993, 36, 3129-3136.
Hwang, J. et al., "Lysosomal enhancement promotes functional recovery in the APPswe/PS1dE9 mouse model of Alzheimer's disease", Oasis-Online Abstract Submission and Invitation System Nov. 4, 2007, Program # 157.12/U23.
Kempf, Dale J. et al., "Evaluation of Substituted Benzamides As P2 Ligands for Symmetry-Based Inhibitors of HIV Protease", Bioorganic & Medicinal Chemistry Letters 1995, vol. 5, No. 22, pp. 2725-2728.
Kick, Ellen K. et al., "Structure-based design and combinatorial chemistry yield low nanomolar inhibitors of cathepsin D", Chemistry & Biology 1997, vol. 4, No. 4, pp. 297-307. Kikuchi, Hitoshi et al., "Spinal cord endoplasmic reticulum stress associated with a microsomal accumulation of mutant superoxide dismutase-1 in an ALS model", PNAS Apr. 11, 2006, vol. 103, No. 15, 6025-6030.
Lee, He-Jin et al., "Clearance of a-Synuclein Oligomeric Intermediates via the Lysosomal Degradation Pathway", The Journal of Neuroscience Feb. 25, 2004, 24(8):1888-1896.
Leliveld, S. R. et al., "Insolubility of Disrupted-in-Schizophrenia 1 Disrupts Oligomer-Dependent Interactions with Nuclear Distribution Element 1 and is Associated with Sporadic Mental Disease", The Journal of Neuroscience Apr. 9, 2008, 28(15):3839-3845.
Mueller-Steiner, Sarah et al., "Antiamyloidogenic and Neuroprotective Functions of Cathepsin B: Implications for Alzheimer's Disease", Neuron Sep. 21, 2006, 51:703-714.
Selkoe, Dennis J. "Alzheimer's Disease is a Synaptic Failure", Science Oct. 25, 2002, vol. 298, pp. 789-791.
Shankar, Ganesh M. et al., "Natural Oligomers of the Alzheimer Amyloid-b Protein Induce Reversible Synapse Loss by Modulating an NMDA-Type Glutamate Receptor-Dependent Signaling Pathway", The Journal of Neuroscience Mar. 14, 2007, 27(11):2866-2875.
Yoshiyama, Yasumasa et al., "Synapse Loss and Microglial Activation Precede Tangles in a P301S Tauopathy Mouse Model", Neuron Feb. 1, 2007, 53: 337-351.

* cited by examiner

*Primary Examiner* — Jennifer M Kim
(74) *Attorney, Agent, or Firm* — Kilpatrick Townsend & Stockton LLP

(57) ABSTRACT

Compounds useful for promoting lysosomal processes and thereby ameliorating the disruption of cellular and functional integrity induced by Aβ and other protein and glycoconjugate species are provided. Methods for the treatment of neurodegenerative diseases that involve protein accumulation and aggregation in the brain, such as Alzheimer's, Parkinson's and Huntington's Disease, are also provided.

10 Claims, 8 Drawing Sheets

COMPOUNDS FOR LYSOSOMAL MODULATION AND METHODS OF USE

CROSS REFERENCE TO RELATED APPLICATIONS

This application claims the benefit of U.S. Provisional Application No. 61/046,294, filed Apr. 18, 2008, which is hereby incorporated by reference.

FIELD OF THE INVENTION

This application relates to the field of medicinal chemistry and more particularly relates to chemical compounds useful as lysosomal modulators.

BACKGROUND

Protein Accumulation Disorders

Many neurological diseases are associated with protein accumulation and aggregation in the brain. For example, Alzheimer's Disease involves accumulation of the Aβ protein, Parkinson's Disease involves accumulation of α-synuclein, Huntington's Disease involves aggregation of mutated huntingtin proteins, and amyotrophic lateral sclerosis involves accumulation of mutated superoxide dismutase-1 proteins. Some chronic psychiatric disorders, such as schizophrenia, bipolar disorder, and recurrent major depression, have also been associated with protein aggregation. The reduction of protein accumulation events is important for slowing the progression of these diseases and disorders. Studies indicate that protein degradation processes that clear these aggregated proteins could provide treatment for some or all of these diseases and disorders.

Alzheimer's Disease

The age-related neurodegenerative disorder Alzheimer's Disease (Alzheimer's) involves the accumulation of oligomeric species, protein aggregation, and altered brain function. One of the major hallmarks of Alzheimer's is the plaque deposits consisting primarily of amyloid fibrils formed by the amyloid beta peptide $A\beta_{1-42}$ as well as the buildup of soluble oligomers of this peptide. Mutations associated with familial Alzheimer's, including mutations in the amyloid precursor protein (APP), strongly implicate $A\beta_{1-42}$ as a causative factor since the mutations increase the relative amount of this Aβ peptide. Increased Aβ is one of the earliest events in Alzheimer's, and, besides extracellular accumulation, Aβ oligomerization also occurs intraneuronally. Aβ oligomers disrupt synaptic plasticity, impair synaptic responses and memory, and cause cytotoxicity, as well as produce synaptic deterioration. Aβ oligomers, especially trimers and multiples of trimeric species, are particularly stable.

There are no current treatments to reduce the abnormal protein accumulation events in Alzheimer's. Only two classes of drugs are approved for treating Alzheimer's, acetyl-cholinesterase inhibitors and N-methyl-D-aspartic acid (NMDA) receptor antagonists. Both types of drugs only affect the symptoms of Alzheimer's. Acetyl-cholinesterase inhibitors are for mild to moderate Alzheimer's and have modest effects in a small percentage of patients who take the drug, and are typically ineffective after 6-12 months of use. The NMDA receptor antagonist that is available treats the secondary pathology but not the protein accumulation in mild to severe Alzheimer's.

Parkinson's Disease

Parkinson's Disease (Parkinson's) is a motor system disorder which is associated with the loss of dopamine-producing brain cells. Dopamine is necessary for coordinated muscle function and movement. Dopamine is normally produced by certain nerve cells (neurons) in the substantia nigra region of the brain; however, Parkinson's patients experience a loss of these neurons which leads to impaired movement. This loss of neurons is associated with the accumulation of alpha synuclein, a protein that is mutated and/or misfolded in Parkinson's and other diseases. The alpha synuclein forms aggregates that accumulate in Lewy bodies, and which are seen in the brains of patients who have died from Parkinson's.

Huntington's Disease

The neurodegenerative disorder Huntington's Disease (Huntington's) is caused by a trinucleotide repeat expansion in the huntingtin gene which codes for huntingtin protein, "Htt." People who have Huntington's Disease have more C-A-G codons on their huntingtin gene which results in Htts that are "altered" or abnormal in that they have an excess number of glutamines. As a result of the excess glutamines, these altered Htts form protein aggregates which can interfere with nerve cell function.

Amyotrophic Lateral Sclerosis

Amyotrophic lateral sclerosis (ALS) is a progressive neurodegenerative disease that attacks nerve cells in the brain and the spinal cord. Neuronal cell death has been linked to the presence of aggregates of mutant superoxide dismutase-1 (SOD1) protein. Mutant SOD1 accumulates to form high molecular weight amorphous aggregates which can interact with other proteins. When these mutant SOD1 proteins accumulate and form aggregates in a neuronal cell, the cell almost always dies.

Chronic Psychiatric Disorders

Studies on patients with phenotypes of affective disorders or schizophrenia have shown that significant fractions of the disrupted-in-schizophrenia (DISC1) protein form aggregates identified as cold Sarkosyl-insoluble protein aggregates. These aggregates do not bind with nuclear distribution element 1 (NDEL1), a key DISC1 ligand, demonstrating a loss of function phenotype. Specifically, in human neuroblastoma cells the aggregates are expression-dependent, detergent-resistant and do not interact with endogenous NDEL1. *Escherichia coli* expresses recombinant (r) NDEL1 which selectively binds to an octamer of an rDISC1 fragment. The rNDEL1 does not bind with dimers or with high molecular weight multimers. Thus, for molecular interaction of DISC1 with NDEL1, an optimum oligomerization exists which is exceeded by aggregation of DISC1. The absence of oligomer-dependent interactions of DISC1 is associated with sporadic mental disease of mixed phenotypes.

Lysosomal Modulation

Lysosomes represent a major degradation pathway necessary for cells to maintain normal protein turnover. The lysosomal pathway is believed to contribute to the clearance of Aβ oligomers, and reduced efficiency in this pathway can have detrimental effects. Administering high dosages of lysosomal inhibitors into brain ventricles of rats, systemically in mice, and to hippocampal slice cultures has been shown to result in the buildup of Aβ species. In addition to Aβ oligomers forming intraneuronally, released Aβ peptide can also be taken up by Alzheimer's-vulnerable neurons causing Aβ accumulation in lysosomes, lysosomal disruption, and the further production of amyloidogenic species. Disturbances in lysosomes have a marked prevalence in Alzheimer's-vulnerable brain regions and are particularly evident in the aged brain, familial Alzheimer's, and related transgenic mouse models.

Lysosomes play an important role in normal protein turnover as well as in clearing and preventing the buildup of misfolded or damaged proteins. Degradation of long-lived proteins and clearance of toxic accumulation events occur in large part via lysosomes, as well as via lysosomes fused with autophagolysosomes of the autophagy pathway. For example, cathepsin is a lysosomal enzyme that cleaves $A\beta_{1-42}$ peptide to smaller non-pathogenic species. This cleavage reduces the amount of $A\beta_{1-42}$ in the brain and contributes to the restoration of synaptic integrity. Overall compromise of lysosomes leads to the accumulation of $A\beta$ and other proteins, and several reports indicate that enhancement of lysosomal function is a plausible strategy to reduce protein accumulation events in several age-related neurodegenerative disorders.

Lysosomes and autophagolysosomes are thought to be activated for the clearance of toxic material. As toxic protein species accumulate, autophagy-lysosomal pathways show clear signs of activation, perhaps as distinct compensatory responses. Responses include autophagic vacuoles and enhanced levels of lysosomal hydrolases including cathepsins B and D. The cathepsin family of lysosomal proteases appears to be particularly responsive to accumulating proteins in neurons. Protein accumulation stress, including that produced by the aggregation-prone $A\beta_{1-42}$ peptide, up-regulates the message, protein, and activity levels of cathepsins. Such responses may keep protein accumulation events partially in check and account for the gradual nature of the associated pathology that can extend over many years in Alzheimer's patients. Cathepsin B, in particular, is a lysosomal enzyme found to reduce $A\beta_{1-42}$ deposition by cleaving the peptide into non-pathogenic species.

Many studies indicate that induction of protein degradation processes occurs as an attempt to clear $A\beta$ and tau species in Alzheimer's, α-synuclein in Parkinson's Disease, and mutant huntingtin in Huntington's Disease. Lysosomal responses are also common among lysosomal storage disorders (LSDs). Mutations that cause specific enzyme deficiencies account for most of these diseases. Metabolically mutated animals comparable to Niemann-Pick Disease and Gaucher's Disease exhibit elevated activities of several lysosomal hydrolases during cellular accumulation events. In addition, mannose 6-phosphorylated glycoproteins and hydrolases were found elevated in the brain in juvenile neuronal ceroid lipofuscinoses. The increased lysosomal enzyme activities are a likely indicator of cellular responses aimed at compensating for accumulating material. It is of interest that caloric restriction enhances protein clearance processes through the increased expression of lysosomal enzymes, and the same treatment improves brain function in a LSD model.

Protein accumulation has been shown to increase the expression of cathepsins, and this response allows for more efficient protein clearance. Such compensatory responses may delay overt neurodegeneration and account for the gradual nature of protein accumulation pathology that can extend over months or years in model systems and years or decades in Alzheimer's. The compensatory response is enhanced by modest levels of certain hydrolase inhibitors, including the cathepsin B and L inhibitor Z-Phe-Ala-diazomethylketone (PADK), making up a class of compounds deemed lysosomal modulators. The induced enhancement of lysosomal capacity has been found to far exceed the mild inhibitory action of PADK, thereby promoting the clearance of PHF-tau and other dementia-related proteins, re-establishing microtubule integrity and microtubule-based transport, and restoring synaptic markers in a brain slice model of protein accumulation pathology.

Drugs that increase lysosomal capacity promote clearance of protein species related to $A\beta$ and tau that accumulate in Alzheimer's Disease and are valuable for treating accumulation events in Parkinson's, Huntington's, and other diseases and disorders. Moreover, enhanced clearance is associated with the restoration of synaptic integrity which is vital for neuronal communication mechanisms underlying memory function as well as neuronal maintenance. Lysosomal modulation represents a unique pharmacological strategy against Alzheimer's. Lysosomal modulators have several advantages over prior art methods: (1) they are first-in-class drugs for treating neurodegenerative disorders either alone or in combination with current treatments; (2) they promote clearance of a broad array of potentially pathogenic proteins (as compared to the host of strategies being developed to reduce $A\beta$ or tau accumulations exclusively); and (3) the drugs repair multiple types of synapses important for memory (as compared to current treatments that act on cholinergic synapses only).

At very high levels PADK can have the opposite effect—i.e. can shut down lysosomal function and cause neuronal compromise. Thus, there is a need for lysosomal modulators that are less toxic, which would provide a safety margin between therapeutic dose and the dose that causes adverse effects. Furthermore, PADK is a peptidic compound and is likely to be unable to be used in vivo due to being rapidly metabolized and unable to penetrate the central nervous system.

Accordingly, lysosomal modulators are provided that are non-peptidic, have increased efficacy, demonstrate a better safety profile, and have improved stability, aqueous solubility, and bioavailability.

SUMMARY OF THE INVENTION

Compounds useful as lysosomal modulators and methods of synthesizing and using those compounds are described herein. The compounds described herein are aimed at slowing, halting, or reversing the progressive synaptic decline and associated cognitive dysfunction in Alzheimer's Disease, Parkinson's Disease, Huntington's Disease, ALS, and other neurological diseases and chronic disorders, including chronic psychiatric disorders, associated with protein aggregation. These compounds are also useful for delaying or preventing disease onset. These small molecule modulators can enhance lysosomal processes in a controlled manner.

Compounds disclosed herein include compounds of the formula (I):

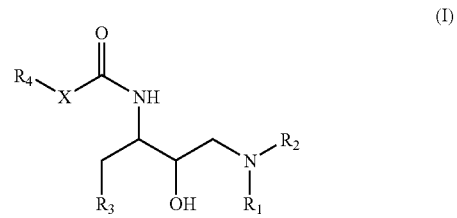

where $R_1$, $R_2$, $R_3$, and $R_4$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

Preferred embodiments include compounds of the formula (II)

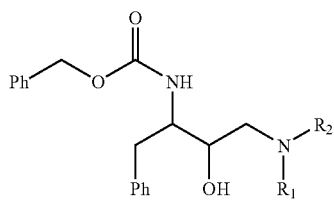

(II)

where $R_1$ and $R_2$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

In more preferred embodiments, $R_1$ and $R_2$ are independently hydrogen; acyl; or substituted or unsubstituted aromatic, heteroaromatic, cyclic aliphatic, or heterocyclic aliphatic rings. In particularly preferred embodiments $R_1$ is a benzyl group or a napthylmethyl group and $R_2$ is either hydrogen or is selected from the group consisting of acetyl, diazoacetyl, and benzoyl groups.

Compounds disclosed herein also include compounds of the formula (III)

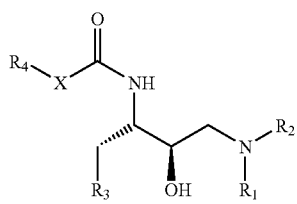

(III)

where $R_1$ and $R_2$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

Preferred embodiments include compounds of the formula (IV)

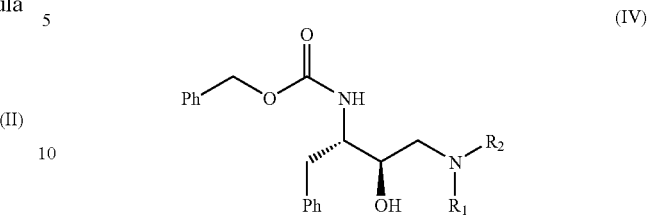

(IV)

where $R_1$ and $R_2$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

In more preferred embodiments, $R_1$ and $R_2$ are independently hydrogen; acyl; or substituted or unsubstituted aromatic, heteroaromatic, cyclic aliphatic, or heterocyclic aliphatic rings. In particularly preferred embodiments $R_1$ is a benzyl group or a napthylmethyl group and $R_2$ is either hydrogen or is selected from the group consisting of acetyl, diazoacetyl, and benzoyl groups.

Preferred lysosomal modulators exhibit the activities of PADK and PPDK. In a preferred embodiment, the lysosomal modulator is a non-peptide compound containing some of the chemical characteristics of PADK or PPDK. Examples of lysosomal modulators described herein include (2R,3S)-3-Cbz amino-2-hydroxy-4-phenyl-1-benzylamino butane (BW1001), (2R,3S)-3-Cbz amino-2-hydroxy-4-phenyl-1-(N-benzyl acetamido) butane (BW1002), (2R,3S)-3-Cbz amino-2-hydroxy-4-phenyl-1-(N-benzyl-2-diazo-ethanamido) butane (BW1003), (2R,3S)-3-Cbz amino-2-hydroxy-4-phenyl-1-(N-naphthylmethyl acetamido) butane (BW1004), and (2R,3S)-3-Cbz amino-2-hydroxy-4-phenyl-1-(N-benzyl benzamide) butane (BW1005). In one preferred embodiment the lysosomal modulator is BW1002 or BW1005.

DETAILED DESCRIPTION OF THE INVENTION

Figure 1:
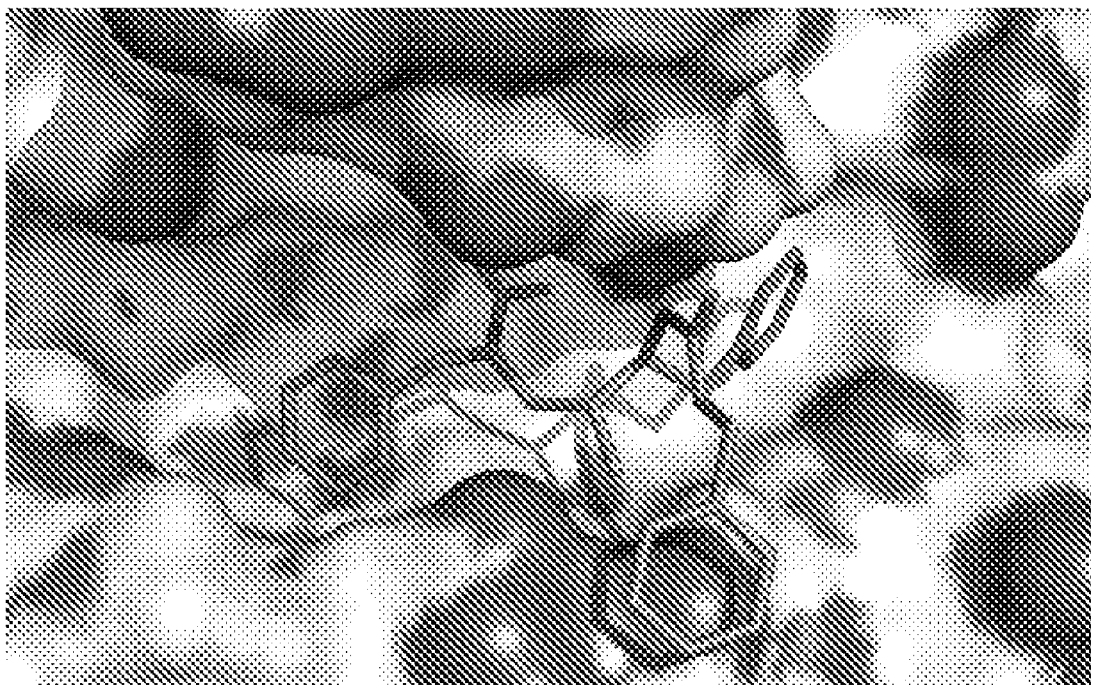
FIG. 1 is a simulation of BW1002 docking to the crystal structure of cathepsin B.

Compounds useful to modulate lysosomal processes and thereby ameliorate protein accumulation-induced disruption of cellular and functional integrity are described herein. These compounds have increased efficacy, stability, improved aqueous solubility, and improved bioavailability over known compounds. Also described herein are methods of synthesizing and methods of using those compounds.

The compounds provided herein have been found to function as lysosomal modulators. Enhancement of lysosomal degradation processes has been shown to reduce the presence of Aβ species and PHF-tau that cause neuronal compromise. Positive lysosomal modulation is one approach to enhancing protein clearance, and such lysosomal modulation has been achieved by safely up-regulating lysosomal enzymes in vivo in rats and mice. Lysosomal modulatory drugs represent a unique strategy to offset protein accumulation events, and they are first-in-class drugs for treating Alzheimer's either alone or in combination with current treatments. The drugs are useful for treating other protein accumulation diseases and disorders, such as Parkinson's and Huntington's, and may also be useful for the treatment of ALS, as well as lysosomal storage diseases and some chronic psychiatric disorders. The drugs promote clearance of a broad array of potentially pathogenic proteins (as compared to a host of strategies being developed to reduce Aβ or tau accumulations exclusively). Additionally, the drugs repair multiple types of synapses important for memory (as compared to current treatments, e.g. Aricept® and Exelon™ Alzheimer's treatments, that act on cholinergic synapses only).

Increased lysosomal enzyme activities are an indicator of cellular responses aimed at compensating for accumulating material. Evidence of compensatory up-regulation of lysosomal enzymes in response to lysosome stress and protein accumulation has led to the identification of a pharmacological avenue for promoting such responses. This pharmacological avenue has been used to identify and synthesize the compounds described herein, which are effective as lysosomal modulators. The base structures of PADK and Z-Phe-Phe-diazomethylketone (PPDK) were used for the design of new lysosomal modulators because PADK and PPDK enhance cathepsin levels at 0.3-10 μM, resulting in 70-80% recovery of synaptic markers that were lost in a protein accumulation model. Other modulators, including diazoacetyl-DL-2-aminohexanoic acid methyl ester, require up to 30 μM to produce neuroprotective effects, but result in only 24-42% synaptic recovery. In vivo studies of PADK modulation show that lysosomal capacity can be enhanced in a dose-dependent manner over long periods without signs of toxicity.

The compounds described herein were designed by probing structure-activity relationships of PADK to determine ways of enhancing efficacy, stability, aqueous solubility, and bioavailability. These structure-activity studies also gave insight into the mechanisms of lysosomal modulation by PADK and its derivatives. Specifically the structure-activity studies probed the relationships between the ability to induce the most therapeutically beneficial lysosome modulation and potency of cathepsin inhibition (e.g. D versus B); cathepsin isozyme selectivity; and key physiochemical parameters.

Three sites on the PADK molecule were targeted for diversification. The three domains were screened in series by varying, one at a time, the Cbz group and the two hydrophobic side chains. The first generation modulator library included a diverse array of functionality with an emphasis on groups that improved on predicted pharmacokinetic parameters.

One disadvantageous structural component of PADK is the central peptide linkage. Peptide linkages in therapeutic agents are known to greatly compromise the bioavailability of those drugs. Therefore, the lysosomal modulators provided herein are non-peptidyl compounds that exhibit activities of known peptidyl lysosomal modulators, such as PADK.

The preferred embodiments include alternative diazoamide traps or alternative electrophilic traps which have not previously been used on these types of mimetics. Like diazoketones, diazoamides are quite stable but should react in a way that is analogous to PADK. The non-peptide lysosomal modulators provided herein are prepared from a chiral azido intermediate based upon slight variation to published routes. Reduction/acylation of the azide and substitution of the nosylate introduce the remaining side chains. Final installation of a diazoamide takes place through the action of the Badet reagent on the secondary amine.

The compounds disclosed herein may be used to treat protein accumulation diseases and disorders in animals including, but not limited to, Alzheimer's Disease, Parkinson's Disease, Huntington's Disease, ALS, schizophrenia, bi-polar disorder, recurrent major depression, and lysosomal storage diseases. Any of the compounds may be administered to the animal as a formulation including the compound and a pharmaceutically acceptable carrier. The formulation may also include excipients, stabilizers, solublizers, or mixtures thereof.

The compounds provided herein, may be administered through different routes, including but not limited to, oral, including buccal and sublingual, rectal, parenteral, aerosol, nasal, intramuscular, intraperitoneal, intravascular, subcutaneous, intradermal, and topical. They may be administered in different forms, including but not limited to solutions, emulsions and suspensions, microspheres, particles, microparticles, nanoparticles, and liposomes. In preferred embodiments the compounds are administered orally.

Compounds disclosed herein include compounds of the formula (I):

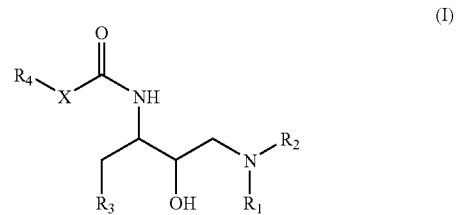

where $R_1$, $R_2$, $R_3$, and $R_4$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

Preferred embodiments include compounds of the formula (II):

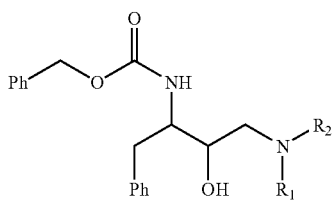

where $R_1$ and $R_2$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

In more preferred embodiments, $R_1$ and $R_2$ are independently hydrogen; acyl; or substituted or unsubstituted aromatic, heteroaromatic, cyclic aliphatic, or heterocyclic aliphatic rings. In particularly preferred embodiments $R_1$ is a benzyl group or a napthylmethyl group and $R_2$ is either hydrogen or is selected from the group consisting of acetyl, diazoacetyl, and benzoyl groups.

Compounds disclosed herein also include compounds of the formula (III):

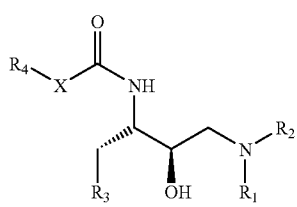

where $R_1$ and $R_2$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S.

Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

Preferred embodiments include compounds of the formula (IV):

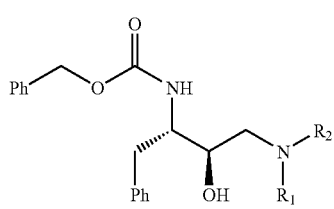

where $R_1$ and $R_2$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring; and where X is a heteroatom including but not limited to O, N, or S. Substituted means having one or more atoms replaced with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl.

In more preferred embodiments, $R_1$ and $R_2$ are independently hydrogen; acyl; or substituted or unsubstituted aromatic, heteroaromatic, cyclic aliphatic, or heterocyclic aliphatic rings. In particularly preferred embodiments $R_1$ is a benzyl group or a napthylmethyl group and $R_2$ is either hydrogen or is selected from the group consisting of acetyl, diazoacetyl, and benzoyl groups.

In the most preferred embodiments the compounds are BW1002, BW1004, or BW1005.

Two of these compounds, BW1004 and BW1005, were designed specifically to improve interaction with the active site of cathepsin B. The docking of lysosomal modulator BW1002 to the crystal structure of cathepsin B was simulated to gain insight into the mode of binding and ascertain the presence of additional opportunities to improve the potency of the lead compound. FIG. 1 depicts this simulation. In this simulation, Bovine cathepsin B was used as the receptor model (PDB: 1QDQ), and was prepared by adding hydrogens, calculating charges, and checking geometries. Flexible docking of BW1002 was carried out with Surflex-Dock as implemented through Sybyl 7.3 software, demonstrating an excellent fit with low ligand conformational energy. The hydrophobic pocket is formed largely by cathepsin B residues Trp 221, His 119, Val 176, Leu 181, and Phe180.

The docked modulator complex showed that there is a very large hydrophobic pocket that is only partially occupied by the N-benzyl and acetyl groups of BW1002. Thus, molecules with larger hydrophobic groups, such as BW1004 and BW1005, should have greater binding interactions with cathepsin B.

EXAMPLES

Potency of PADK, PPDK and Selected Non-Peptide Lysosomal Modulators

PADK, PPDK, and several non-limiting examples of the non-peptide lysosomal modulators provided herein, including BW1001, BW1002, BW1003, BW1004, and BW1005, were screened in hippocampal slice cultures to determine their potencies. The structures of these compounds and their potencies are shown in Table 1 below. The cultured slices were treated daily with different modulator concentrations for 3-6 days. As listed in Table 1, BW1004 and BW1005 increased levels of cathepsin D with potencies at or near that of PADK. For these two compounds, improved potency did not appear to be associated with increased $C_{log}P$ values. BW1001 was not tested further due to its low potency.

TABLE 1

| Name | Structure | $C_{log}P$ | $EC_{50}$ | $EC_{2\text{-}fold}$ |
|---|---|---|---|---|
| PADK | 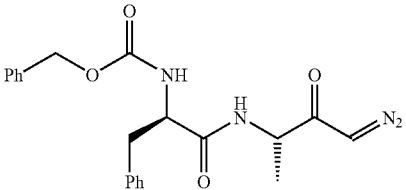 | 1.60 | 10 μm | 3.2 μM |
| PPDK | 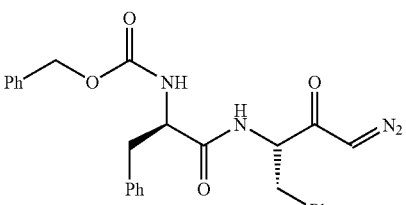 | 1.90 | 14 μm | ~5 μM |
| BW1001 | 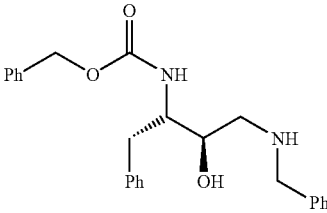 | 4.06 | 20 μM | |
| BW1002 | 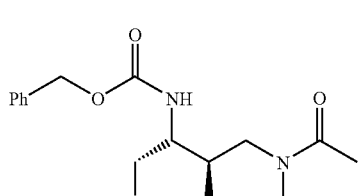 | 3.83 | 3 μM | ~1 μM |
| BW1003 | 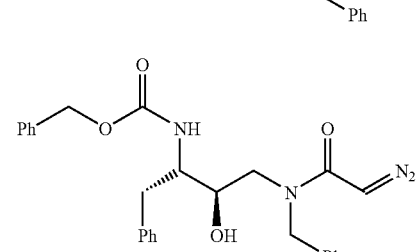 | 3.05 | 2.0 μM | |
| BW1004 | 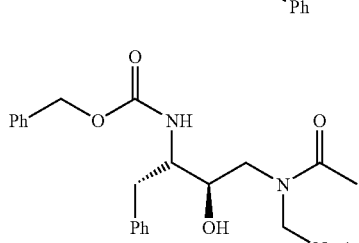 | 5.01 | 20 μM | |

TABLE 1-continued

| Name | Structure | $C_{log}P$ | $EC_{50}$ | $EC_{2-fold}$ |
|---|---|---|---|---|
| BW1005 | (structure shown) | 4.99 | 15 μM | |

Toxicity of PADK, PPDK, and Selected Non-Peptide Lysosomal Modulators

Potential toxicity was tested by assessing synaptic markers and subjecting media samples from the treated slice cultures to a standard LDH assay. PADK, BW1002, BW1005, and other modulators did not cause synaptic decline or LDH release. Only BW1003 exhibited evidence of a time-dependent increase in LDH activity apparently released from damaged cells. However, the increase in LDH release after 6 days of BW1003 treatment only approached significance, and only represented <2% of the maximal LDH release produced by total cellular disruption (using 1% TX-100). BW1003 also caused evident synaptic decline when measuring pre- and postsynaptic markers in the treated slice samples. B1003 was not pursued due to its potential toxicity. Other non-peptide lysosomal modulators, including BW1004 and BW1005, did not produce evident toxicity in the slice model using the LDH assay or synaptic marker assessment.

Lysosomal Modulation In Vitro

In vitro testing of PADK

Clearance of Accumulated Proteins

Figure 2:
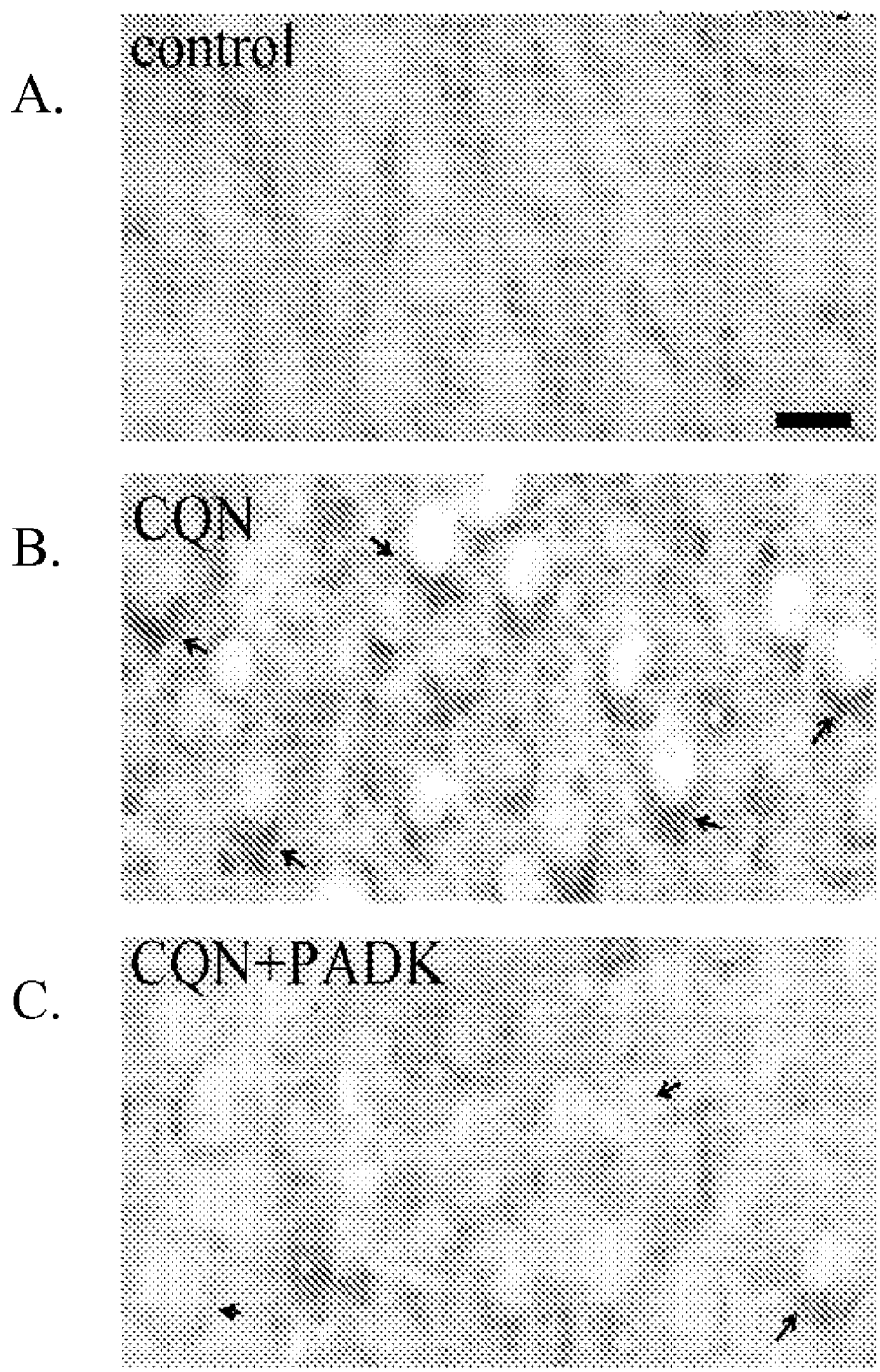
FIGS. 2A-C are immunostains of hippocampal slice cultures for human paired helical filaments (PHFs).

The chloroquine-induced hippocampal slice model of protein accumulation was used to show that lysosomal modulators promote clearance of pre-existing protein accumulations. The slice model exhibits intraneuronal deposition of PHF-immunopositive material, an increase in carboxyl-terminal fragments of APP, as well as a gradual loss of synaptic components. FIGS. 2A-C are immunostains of hippocampal slice cultures for human paired helical filaments (PHFs). The pathogenic PHF was undetectable in control tissue, FIG. 2A, whereas cellular accumulation of PHF was evident after 6 days of chloroquine treatment followed by 2 days of washout, FIG. 2B. When PADK was included in the washout infusion, the chloroquine-induced deposits in CA1 neurons were markedly reduced. In contrast, removal of chloroquine and treatment with 3 μM PADK for 2 days resulted in clearance of most neuronal deposits of PHF material as shown in FIG. 2C. Size bar: 16 μm.

In Vitro Testing of Non-Peptide Lysosomal Modulators

The non-peptide lysosomal modulators described above were screened in hippocampal slice cultures since that convenient culture system possesses native circuitries and is well suited for parallel analyses of cathepsins and synaptic markers which exhibit compensatory responses and synaptic vulnerability as found in vivo.

Activation of Lysosomal Enzymes

The hippocampal slices were maintained in culture for 10-12 days to stabilize, then were treated daily with different modulator concentrations for 3 days. Then they were harvested rapidly in ice-cold buffer and homogenized in the presence of protease inhibitors.

Figure 3:
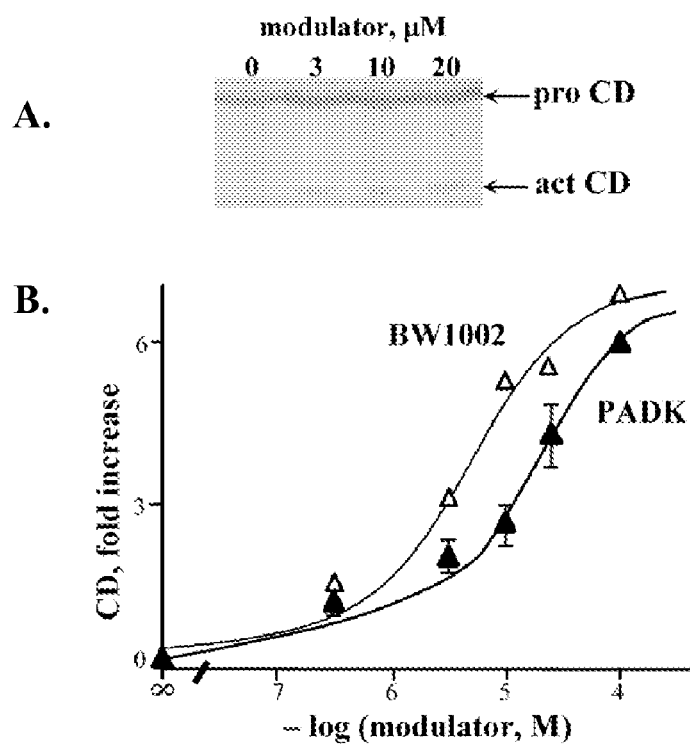
FIG. 3A is an immunoblot showing modulator-induced increases in the proform and active form of cathepsin D in hippocampal slice cultures.
FIG. 3B is a graph showing the dose-dependent up-regulation of cathepsin D in hippocampal slice cultures by PADK and by BW1002.

Equal protein aliquots of the slice samples were subjected to immunoblotting to label the proform and the active form of cathepsin D (CD). Results of this testing are shown in FIG. 3. FIG. 3A is an immunoblot showing PADK induced increases in the proform and active form of cathepsin D in hippocampal slice cultures. FIG. 3B is a graph showing the dose-dependent up-regulation of cathepsin D in hippocampal slice cultures by PADK and by BW1002. The titration curves in FIG. 3B show that BW1002 exhibited more potent lysosomal enhancement than PADK. Both the proform and the active form of cathepsin D were increased by both PADK and the non-peptidyl lysosomal modulator BW1002, which is assumed to be more stable than PADK; the actin load control was routinely found to be unchanged. BW1002 is more potent than PADK as shown by the $EC_{50}$ as well as the concentration needed for a 2-fold increase in cathepsin levels ($EC_{2-fold}$), both of which are listed in Table 1. Improved potency appears to correspond with increases in $C_{log}$ P. PADK has an $EC_{2-fold}$ value of 3.2 μM, whereas the $EC_{2-fold}$ value for BW1002 is approximately 1 μM.

Clearance of Accumulated Proteins

Figure 4:
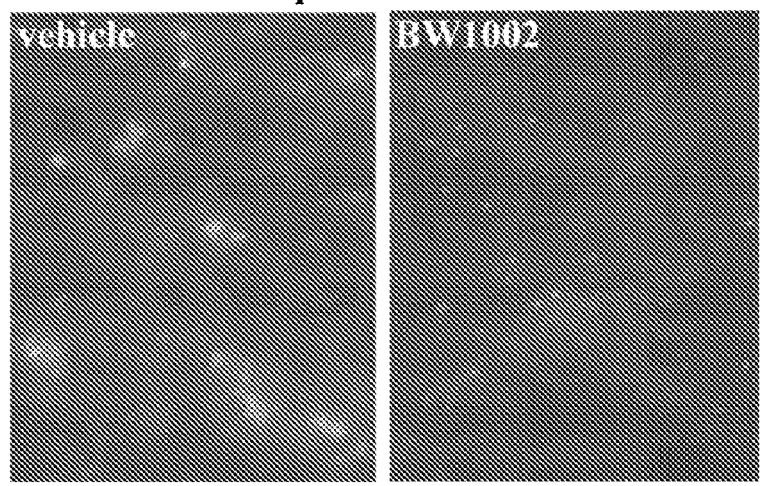
FIGS. 4A-B are immunostains showing the effect of treating a hippocampal slice culture previously infused with chloroquine with vehicle or with BW1002.

The BW1002 compound was also tested for enhanced protein clearance in a slice model of Alzheimer's-type protein accumulation. Hippocampal slice cultures were infused with the lysosomal disruptor chloroquine for 6 days in order to induce accumulation of material labeled by the anti-$A\beta_{1-42}$ antibody. Hippocampal slice cultures, when subjected to chloroquine-induced protein accumulation stress, exhibited accumulated Aβ peptides, PHF-tau aggregates, as well as Alzheimer's-type synaptic pathology. As in the case with several transgenic mouse models of Alzheimer's, a striking resemblance is apparent between the human disease state and chloroquine-treated slices with regard to loss of synaptic integrity as well as with respect to early transport failure and axonopathy. Hippocampal slice cultures were infused with the lysosomal disruptor chloroquine for 6 days in order to induce accumulation of material labeled by anti-$A\beta_{1-42}$ antibody. Chloroquine was then removed and the slices treated with vehicle or 5 μM BW1002 for 2 days. FIGS. 4A-B are immunostains that show the effect of this treatment. Immunostaining in CA1 was reduced by the lysosomal modulator (view-width: 60 μm). As compared to FIG. 4A, FIG. 4B shows that immunolabeling of protein accumulation events in CA1 was reduced by the lysosomal modulator (view width: 60 μm). Thus, the lysosomal modulator BW1002 promotes clearance of the accumulated material in the slice model.

Figure 5:
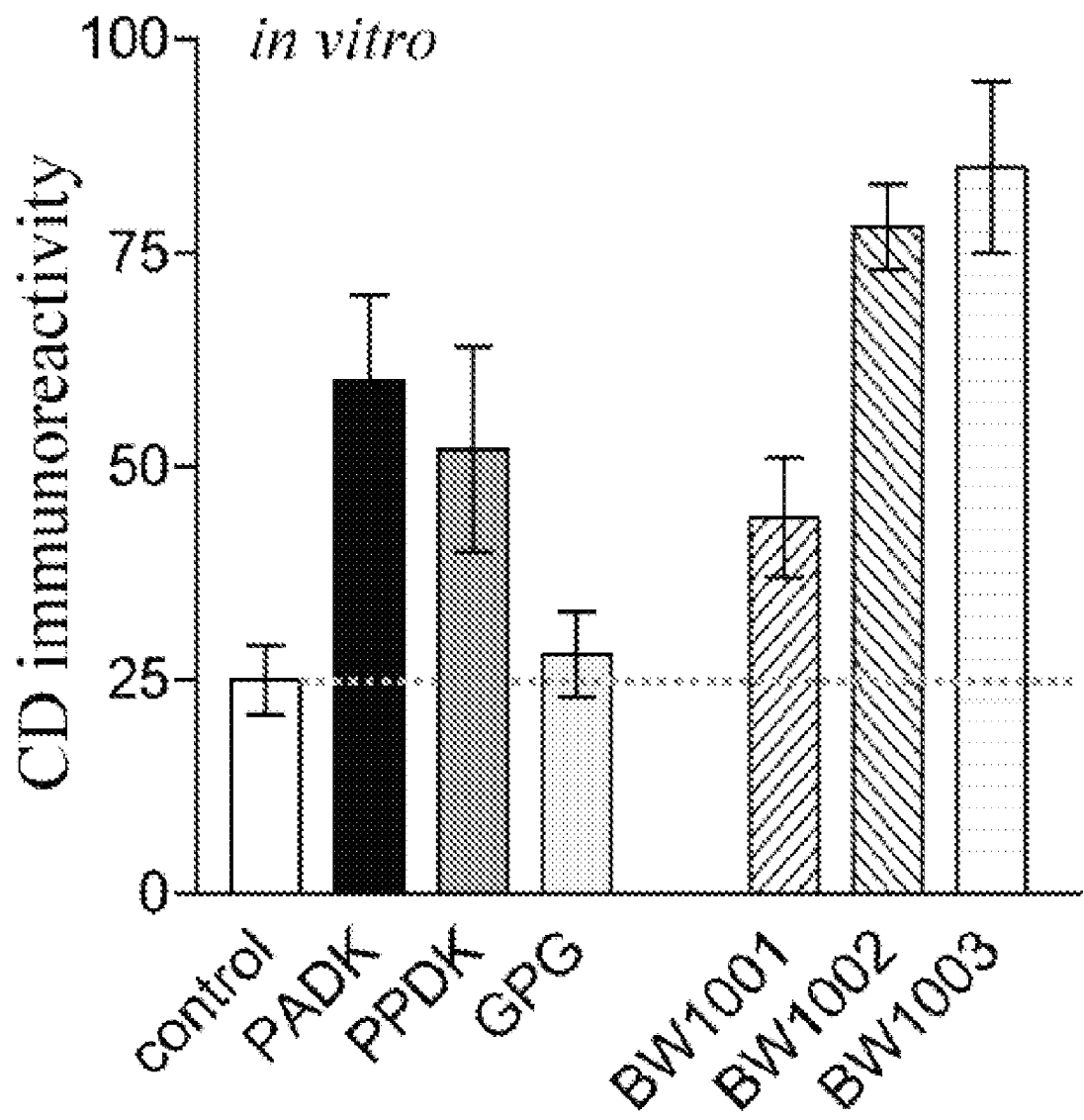
FIG. 5 is a bar graph showing cathepsin D immunoreactivity in mice in response to PADK, other peptidyl compounds, and non-peptidyl lysosomal modulators.

Comparison of Activation of Lysosomal Enzymes by Peptidal and Non-Peptidal Compounds Peptidyl compounds PADK, PPDK, the cathepsin B inhibitor glycyl-phenylalanyl-glycine-aldehyde semicarbazone (GPG) and non-peptidyl lysosomal modulators BW1001, BW1002, and BW1003 were tested using the slice model and compared. Slices were treated daily for 3 days with 10 μM compound, then harvested rapidly for immunoblot assessment of active CD levels (ANOVA: P<0.0001). FIG. 5 is a bar graph showing the results of these tests. The data in FIG. 5 indicate that the non-peptide lysosomal modulators provide potent lysosomal modulation that enhances clearance of pathogenic accumulations. All data represent means±SEM.

Lysosomal Modulation In Vivo
In vivo testing of PADK
Activation of Lysosomal Enzymes It is known that PADK elicits lysosomal modulation in vivo, resulting in significant increases in rat brain levels of cathepsins B and D. In 10-12-month old mice, 9 daily PADK intraperitoneal (i.p.) injections were also found to cause a dramatic increase in immunostaining for the active form of cathepsin B in hippocampal cells positive for the neuronal marker NeuN. The enhanced cathepsin staining was evident in many brain regions and co-localized with the lysosomal marker LAMP-1.

The modulator PADK up-regulates cathepsins without causing adverse effects. Hippocampal homogenates were assessed for the mice. FIGS. 6A-D are graphs showing the effects of PADK doping on various biological and physical attributes of 10 month old mice.

Figure 6:
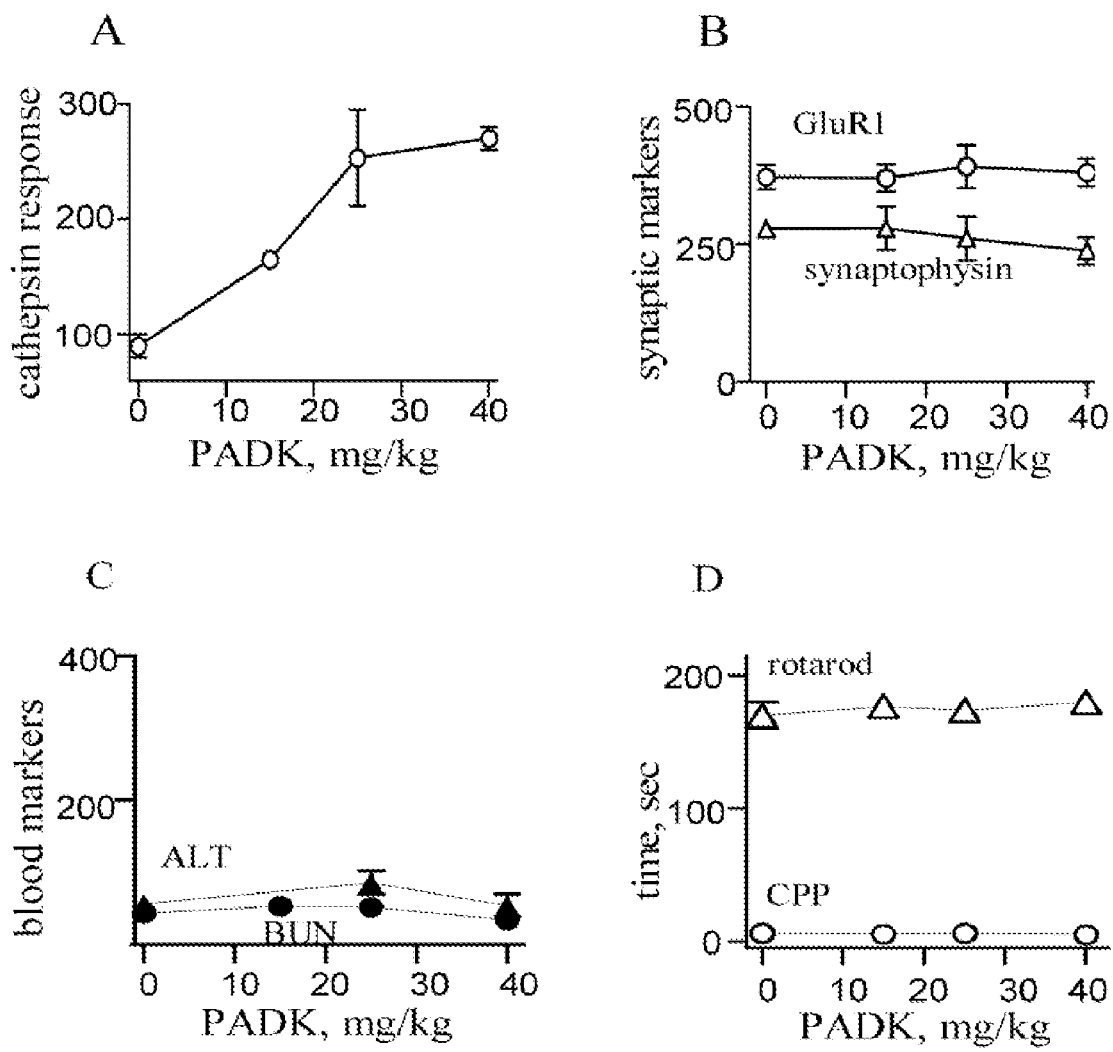
FIGS. 6A-D are graphs showing the effects of PADK dosing on various biological and physical attributes of 10 month old mice.

Across different dosages, PADK produced dose-dependent increases in cathepsin levels as shown in FIG. 6A, which is a graph showing the up-regulation effect by PADK dosing on cathepsin. No adverse effects were evident on synaptic markers GluR1 and synaptophysin, as shown in FIG. 6B. ALT, which indicates damage to liver function, and BUN, which indicates kidney compromise, were measured with PADK dosing and, as shown in FIG. 6C, no change in either ALT or BUN was seen with the PADK dosing. Finally, the PADK dosing did not impair motor skills, coordination, or spatial memory in the mice. FIG. 6D is a graph showing the results of motor skills and spatial memory tests. Motor skills and coordination were assessed using a variable-speed rotating rod and measuring the time the animal could remain moving on the rod. Spatial memory was tested with a conditions place preference (CPP) North-South paradigm in which the animal must remember where a previous reward was presented. Thus, the lysosomal modulation occurred in the absence of any evident effects on liver/kidney integrity, blood urea levels, or on normal brain functionality.

In-Vivo Testing of Non-Peptide Lysosomal Modulators
Synaptic Protection by PADK and Non-peptide Lysosomal Modulators Modulator BW1005, was administered daily i.p. into an Alzheimer's Disease model —PDGF-APP$_{SwInd}$ transgenic mice. The transgenic mice are hemizygotes for a mutant form of the human APP gene containing both the Swedish (K670N/M671L) and the Indiana (V717F) mutations (APP$_{SwInd}$). Our previous work showed that the hemizygote mice express the human APP transgene product in the neocortex and hippocampus, while control non-transgenic mice do not express the human protein. Based on its potency in relation to PADK's effect in slices and mice, BW1005 was injected i.p. daily at a dose of 45 mg/kg. Since BW1002 is more potent than BW1005 in the slice model, additional mice were injected with the BW1002 compound at 25 mg/kg.

Figure 7:
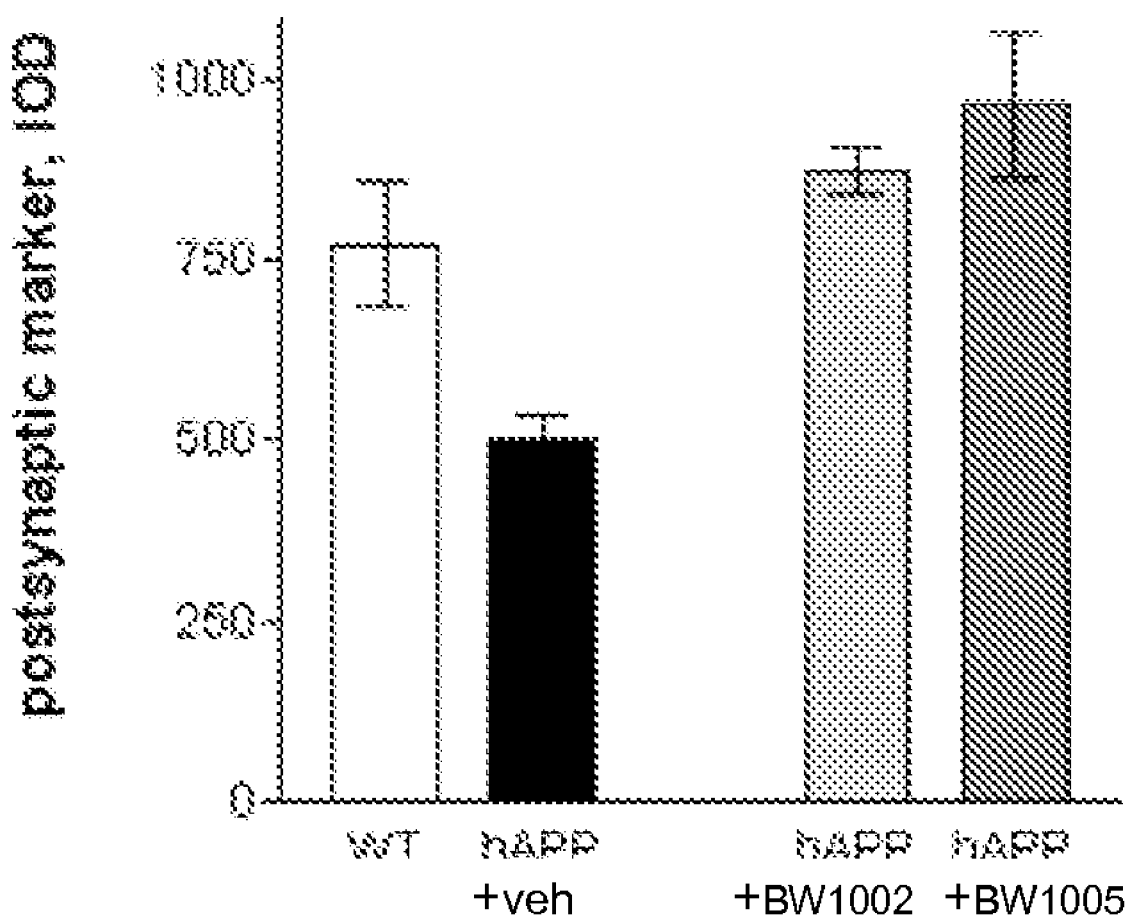
FIG. 7 is a bar graph showing the mean synaptic marker GluR1 for mice treated with vehicle and with either BW1002 or BW1005.

The brains of the mice were dissected and assessed for the postsynaptic marker GluR1. The transgenic mouse model exhibits a deficit in GluR1 as compared to wild-type mice, and the new lysosomal modulators promoted recovery of the marker. FIG. 7 is a bar graph showing the mean GluR1 measure ±SEM for each group studied (post hoc test: p=0.05). The bar graph in FIG. 7 indicates that both BW1002 and BW1005 provided significant synaptic protection. Changes in cathepsin levels may explain the synaptic protection.

Behavioral Testing—Novel Arm Paradigm

Figure 8:
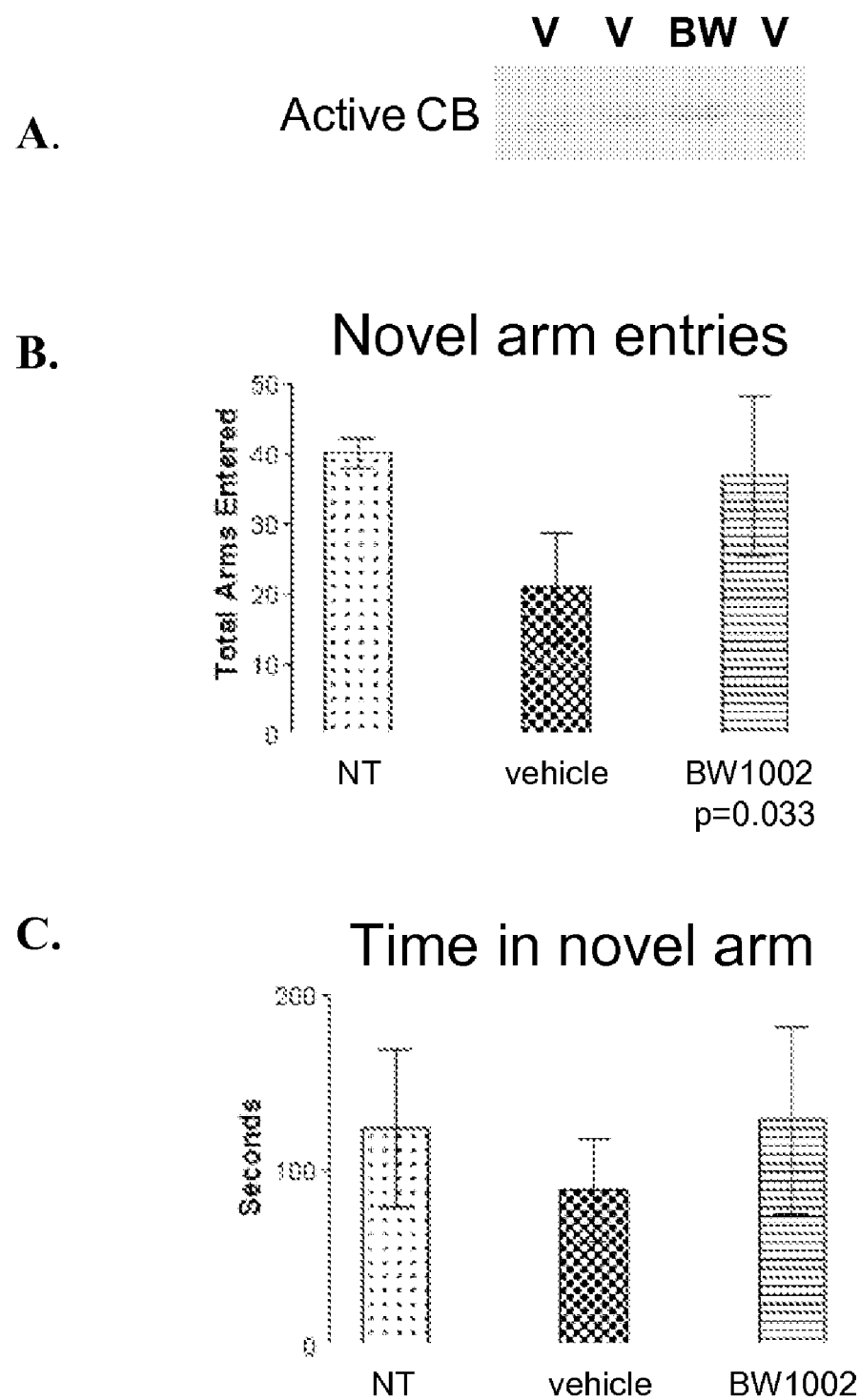
FIG. 8A is an immunoblot showing the active form of cathepsin B in the brains of mice treated with BW1002.
FIGS. 8B-C are bar graphs showing the results in a novel arm paradigm for mice treated with vehicle or with BW1002.

Aged mice exhibit the kind of synaptic deficits that contribute to behavioral dysfunction. Non-treated young mice (NT) and aged mice treated daily with either vehicle (V) or BW1002 (BW) were evaluated in a novel arm paradigm. Subsequent preparation of brain homogenates were assessed for the active form of cathepsin B (CB) by immunoblot. BW1002 at 35 mg/kg×10 days was used and tested for lysosomal modulation. Results are shown in FIGS. 8A-C. FIG. 8 is an immunoblot showing evidence of cathepsin B upregulation (active form) in dissected brain tissue. Overall, the 35 mg/kg dosage of BW1002 increased cathepsin B in 4 of 6 mice.

FIGS. 8B-C are graphs showing results of the novel arm paradigm. Briefly, on day 1 animals were allowed to explore a Y maze that only had the right arm open containing colored objects. After 5 min of exploring, mice were returned to their home cage. On day 2, the 5 minute exploring period occurred with both arms open, and animals were assessed for entries and total time spent in the novel left arm of the maze. Animals have a strong tendency to explore a novel environment more than a place they have been before. There is a characteristic age-related deficit in the memory of which maze arm is the novel arm (the novel arm test). Interestingly, data in FIG. 8B indicate that this deficit appears to be eliminated by BW1002. FIG. 8C indicates that, such a result is also suggested when assessing total time spent in the novel arm.

Synaptic Integrity and Behavioral Deficits

Figure 9:
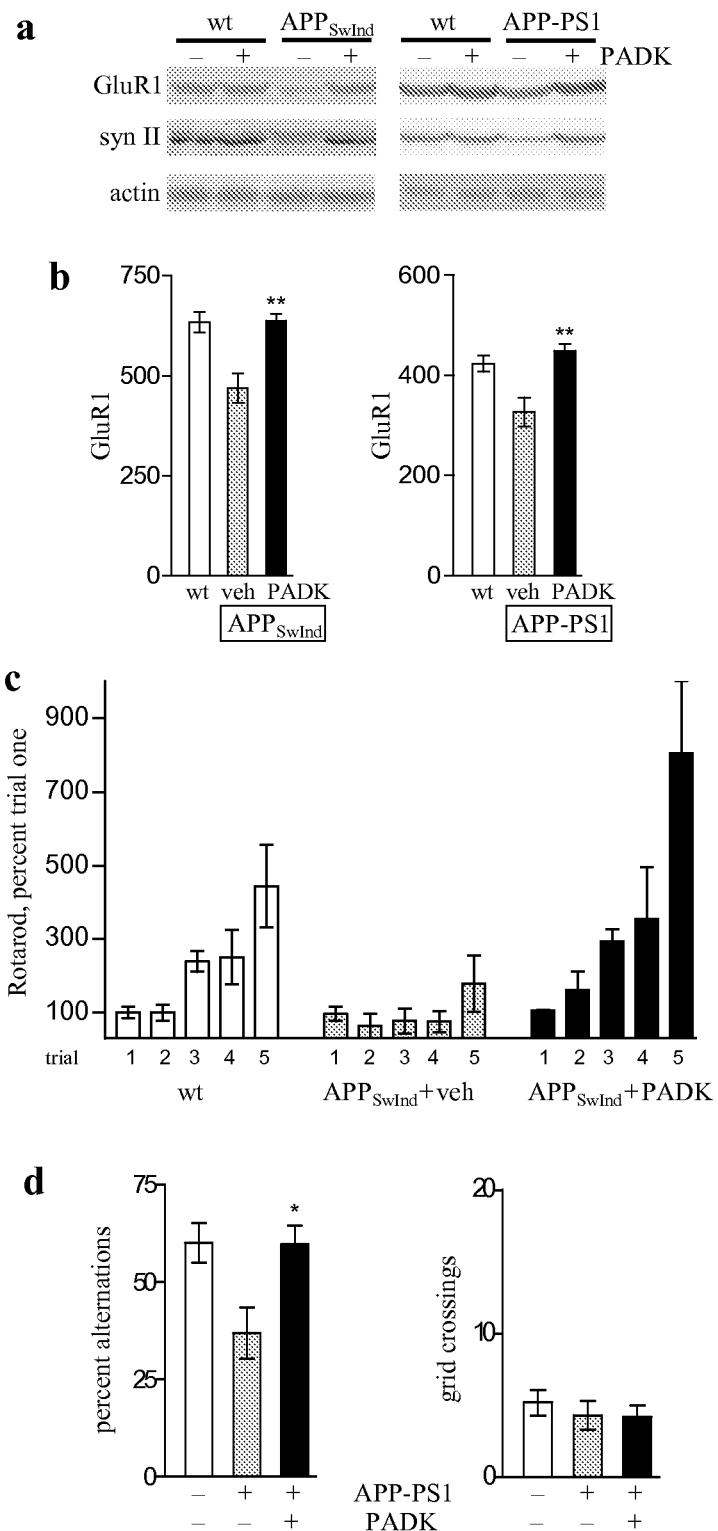
FIG. 9A is an immunoblot showing a comparison of a presynaptic protein and a postsynaptic marker in two different mouse models.
FIGS. 9B-D are graphs showing the results of several tests on mice treated with vehicle and mice treated with PADK.

To compare the BW1002/1005 results to previous PADK work, homogenate samples were analyzed by immunoblot for the presynaptic protein synapsin II and postsynaptic glutamatergic marker GluR1. The results of these analyses are shown in FIG. 9. FIG. 9A shows two immunoblots showing that samples from two different Alzheimer's mouse models exhibited deficits of 23-31% testing APP$_{SwInd}$ and APPswe/PS1ΔE9 mice as compared to age-matched wild-types (P<0.01). FIG. 9B is a bar graph showing that PADK significantly reduced the GluR1 deficit in the two mouse models, reaching levels comparable to those found in non-transgenic control mice (ANOVA: P<0.001; n=12-20). Similar indications of presynaptic protection were found when measuring synapsin II. The synaptic protection of GLuR1 provided by BW1002 and BW1005, described previously, was greater than that provided by PADK.

The improvement of synaptic integrity by PADK was also associated with the reduction of behavioral deficits in the mouse models. FIG. 9C is a bar graph showing rotorod performance for several groups of mice. Vehicle-injected APP$_{SwInd}$ mice showed no improvement in Rotarod performance across 5 trials (P=0.37; n=10), in contrast to the improvement exhibited by age-matched wildtype mice that received vehicle (ANOVA: P=0.0036; n=19) (FIG. 9C). PADK treatment enabled the APP$_{SwInd}$ mice to improve across Rotarod trials conducted on the $8^{th}$ and $9^{th}$ injection days (P<0.0069). FIG. 9D is a bar graph illustrating spontaneous alternation behavior in the second type of Alzheimer's mouse model (APPswe/PS1ΔE9). APPswe/PS1ΔE9 mice treated with vehicle or PADK were tested on the hippocampal-dependent task of spontaneous alternation behavior in a T-maze. The mice were allowed to explore starting from the intersection of a T-maze, and were monitored for the order of entries into the three arms (arms A, B, and C). In control mice, every third explored arm is usually different than the previous two (e.g., A-B-C, B-A-C, etc.; the third decision being an alternation). Alzheimer's mice, on the other hand, frequently go back into one of the previous two arms explored (e.g., A-B-A, C-B-B), thus reducing the percent alternations. The vehicle-treated transgenic mice exhibited reduced alternation behavior as compared to age-matched wildtypes (P<0.0001). The PADK treatment resulted in significantly improved alternations, reaching a performance level equal to that of the non-transgenic control mice. Open field mobility assessment confirmed no change in exploratory mobility across the different groups of mice.

In sum, the lysosomal modulator treatment using compounds described herein led to improved levels of synaptic markers, perhaps by reducing protein accumulation linked to transport deficits, axonopathy, and synaptic compromise, events found in Alzheimer's Disease as well as in the normal aged brain. With appropriate agents screened for effectiveness and safety, lysosomal modulation may provide a treatment strategy for different types of age-related protein accumulation diseases.

Synthesis of Selected Compounds

Preparation of (2R,3S)-3-azido-2-tetrahydrapyranyl-4-phenyl butan-1-yl p-toluene sulfonate (V)

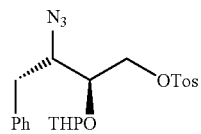

Tosyl alcohol (900 mg, 2.49 mmol) was dissolved in 20 ml of methylene chloride. To this solution, dihydropyran (3.73 mmol) was added dropwise. To this, pyridinium p-toluene sulfonate (PPTS 10 mol %) was added. The reaction mixture was stirred for 24 hrs and it was washed with saturated NaHCO$_3$ solution, dried (Na$_2$SO$_4$), and concentrated under reduced pressure to give a light brown colored oil. It was then subjected to silica gel chromatography with hexane/ethyl acetate (3:1) as eluent to give the THP protected alcohol (V) as an oil and as a mixture of isomers. 1.042 g (94%). $^1$H NMR (500 MHz, CDCl$_3$) δ 7.78-7.89 (m, 4H), 7.15-7.42 (m, 14H), 4.64-4.75 (m, 2H), 4.21-4.34 (m, 4H), 3.71-3.98 (m, 4H), 3.38-3.62 (m, 4H), 2.92-3.02 (m, 2H), 2.63-2.74 (m, 2H), 2.42-2.51 (m, 6H), 1.43-1.94 (m, 12H); $^{13}$C NMR (125 MHz, CDCl$_3$) 139.56.41, 139.30, 137.23, 137.08, 129.20, 129.15, 128.52, 128.46, 128.35, 128.27, 128.13, 128.09, 127.02, 126.88, 126.75, 126.66, 100.28, 99.15, 80.23, 78.84, 66.04, 65.12, 63.91, 63.19, 50.15, 47.99, 37.45, 36.35, 31.08, 31.06, 25.33, 25.24, 21.02, 20.94, 20.43, 19.81.

Preparation of (2R,3S)-3-azido-2-tetrahydrapyranyl-4-phenyl-1-benzyl amino butane (VI)

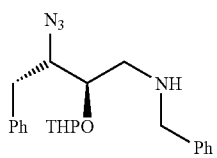

To a solution of tosyl protected alcohol (V) (0.842 g, 1.89 mmol) in anhydrous THF (10 ml), benzylamine (1.05 ml, 9.46 mmol) was added. The reaction mixture was refluxed at 90° C. for 56 hrs, cooled and then concentrated. Chromatography on silica gel with 1:1 hexane/ethyl acetate as eluent gave the product (VI) as two isomers. 485 g (67% yield); $^1$H NMR (500 MHz, CDCl$_3$) δ 7.17-7.29 (m, 20H), 4.66-4.78 (m, 2H), 3.78-4.21 (m, 10H), 3.48-3.58 (m, 2H), 2.84-3.12 (m, 6H), 2.66-2.79 (m, 2H), 1.45-1.98 (m, 12 H); $^{13}$CNMR (125 MHz, CDCl$_3$) 140.41, 140.30, 138.23, 138.08, 129.20, 129.15, 128.62, 128.56, 128.45, 128.37, 128.13, 128.09, 127.02, 126.88, 126.75, 126.66, 100.28, 99.15, 80.23, 78.84, 66.04, 65.12, 63.91, 63.19, 54.09, 53.98, 50.15, 47.99, 37.45, 36.35, 31.08, 31.06, 25.33, 25.24, 20.43, 19.81.

Preparation of (2R,3S)-3-amino-2-tetrahydrapyranyl-4-phenyl-1-benzyl amino butane (VII)

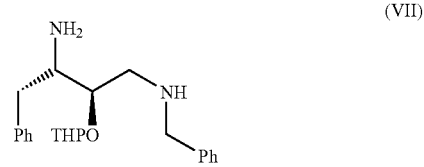

The THP protected benzyl amine (VI) (0.485 g, 1.28 mmol) was dissolved in 8 ml of absolute methanol in a 25 ml flask. The flask was degassed and the contents were cannulated to another 25 ml degassed flask containing 10% Pd/C in 3 ml of absolute methanol. The reaction mixture was then stirred in a hydrogen atmosphere for 12 hrs and then filtered through celite. The solvent was removed under reduced pressure and the residue was purified by silca gel chromatography with 5% methanol in chloroform as an eluent to give the reduced amine (VII) as an oil and as a mixture of isomers. 0.365 g (81%) yield. $^1$H NMR (500 MHz, CDCl$_3$) δ 7.15-7.30 (m, 20H), 4.64-4.76 (m, 2H), 3.78-4.18 (m, 10H), 3.32-3.58 (m, 4H), 2.84-3.12 (m, 4H), 2.66-2.78 (m, 2H), 1.42-1.57 (m, 12H). $^{13}$CNMR (125 MHz, CDCl$_3$) 140.42, 140.30, 138.22, 138.08, 129.20, 129.15, 128.61, 128.56, 128.44, 128.37, 128.13, 128.09, 127.02, 126.88, 126.75, 126.66, 100.28, 99.15, 80.23, 78.84, 66.04, 65.12, 60.18, 60.09, 54.09, 53.98, 50.15, 47.99, 37.43, 36.35, 31.08, 31.06, 25.33, 25.24, 20.41, 19.81.

Preparation of (2R,3S)-3-Cbz amino-2-tetrahydrapyranyl-4-phenyl-1-benzyl amino butane (VIII)

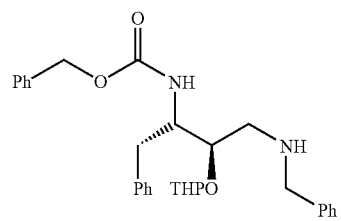

The reduced primary amine (VII) (0.365 g, 1.03 mmol) was taken up in 6 ml of ether along with 3 ml of saturated sodium bicarbonate solution and cooled to 0° C. Then benzyl chloroformate was added dropwise to the reaction mixture and stirred for 5 hours. The aqueous layer was then separated, and the organic layer was dried (Na$_2$SO$_4$) and concentrated under reduced pressure. It was then subjected to silica gel chromatography using 2:1 hexane/ethyl acetate as an eluent to give Cbz protected amine (VIII) as an oil and as a mixture of isomers. 0.490 g (97%) yield. $^1$H NMR (500 MHz, CDCl$_3$) δ 7.08-7.43 (m, 30H), 5.01-5.33 (m, 6H), 4.68-4.84 (m, 2H), 3.74-4.14 (m, 8H), 3.36-3.62 (m, 4H), 2.82-3.10 (m, 4H), 2.66-2.78 (m, 2H), 1.42-1.93 (m, 12H). $^{13}$CNMR (125 MHz, CDCl$_3$) 155.87, 155.78, 140.91, 140.84, 140.42, 140.30, 138.22, 138.08, 129.20, 129.15, 128.74, 128.68, 128.61, 128.56, 128.44, 128.37, 128.13, 128.09, 127.02, 126.88, 127.72, 127.64, 127.43, 127.38, 126.75, 126.66, 100.28, 99.15, 80.23, 78.84, 71.88, 68.59, 66.04, 65.12, 60.18, 60.09, 54.09, 53.98, 50.15, 47.99, 37.43, 36.35, 31.08, 31.06, 25.33, 25.24, 20.41, 19.81.

Preparation of (2R,3S)-3-Cbz amino-2-hydroxy-4-phenyl-1-benzyl amino butane (BW1001) (IX)

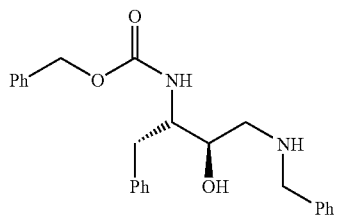

(IX)

The Cbz protected amine (VIII) (0.495 g, 1.02 mmol) was dissolved in 10 ml of ethanol and to this 10 mol % of PPTS added. The reaction mixture was stirred at 60° C. for 5 hrs and was then washed with sat. sodium bicarbonate solution. The organic layer was separated, dried (Na$_2$SO$_4$), and concentrated under reduced pressure. It was then subjected to silica gel chromatography with 2:1 hexane/EtAc as eluent to give the Cbz protected amino alcohol (IX) as an oil. 0.350 g (86%) yield. $^1$H NMR (500 MHz, CDCl$_3$) δ 7.07-7.38 (m, 15H), 5.02-5.35 (m, 3H), 4.52-4.87 (m, 2H), 3.75-4.04 (m, 2H), 3.28-3.49 (m, 1H), 2.75-2.94 (m, 2H). $^{13}$CNMR (125 MHz, CDCl$_3$) 155.85, 140.91, 140.36, 138.22, 129.15, 128.68, 128.56, 128.37, 128.10, 127.72, 127.41, 127.64, 126.75, 80.23, 60.18, 54.14, 50.15, 47.99, 37.43.

Preparation of (2R,3S)-3-Cbz amino-2-hydroxy-4-phenyl-1-(N-benzyl acetamido) butane (BW1002) (X)

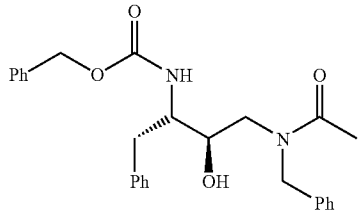

(X)

The Cbz protected amino alcohol (IX) (0.035 g, 0.086 mmol) was dissolved in 1 ml of anhydrous THF. To this triethylamine (0.11 mmol) was added dropwise. After 10 minutes acetic anhydride (0.11 mmol) was added and 1 mg of DMAP was added. The reaction mixture was stirred for 12 hrs and was then washed with water. The organic layer was separated, dried (Na$_2$SO$_4$), and concentrated under reduced pressure. It was then subjected to silica gel chromatography with 2:1 hexane/ethyl acetate as eluent to give the acetylated amino alcohol (X) as an oil. 0.029 g (75%). $^1$H NMR (500 MHz, CDCl$_3$) δ 7.13-7.49 (m, 15H), 5.02-5.37 (m, 3H), 4.52-4.87 (m, 2H), 3.75-4.00 (m, 2H), 3.28-3.51 (m, 1H), 2.75-2.94 (m, 2H), 2.07 (s, 3H). $^{13}$CNMR (125 MHz, CDCl$_3$) 168.4, 155.85, 140.91, 140.36, 138.22, 129.15, 128.68, 128.56, 128.37, 128.10, 127.72, 127.41, 127.64, 126.75, 80.23, 60.18, 54.14, 50.15, 47.99, 37.43, 17.1.

Preparation of (2R,3S)-3-Cbz amino-2-hydroxy-4-phenyl-1-(N-benzyl-3-oxo-butanamido) butane (XI)

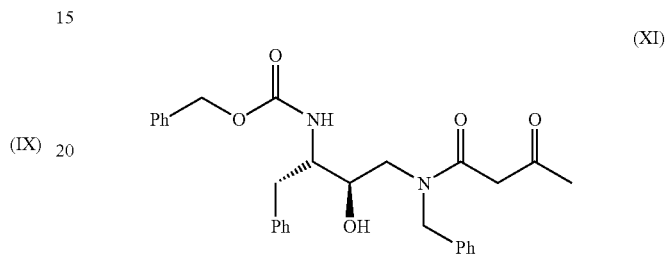

(XI)

The Cbz protected amino alcohol (IX) (0.080 g, 0.19 mmol) was dissolved in 2 ml of ethanol and to this diketene (23 μL, 0.29 mmol) was added dropwise. The reaction mixture was then stirred for 1 hour and diluted with 4 ml dichloromethane. It was then poured into water and the organic layer was separated, and dried (Na$_2$SO$_4$). It was then subjected to silica gel chromatography with 2:1 hexane/ethyl acetate as an eluent to give the keto-amide (XI) as oil. 100 mg (98% yield) $^1$H NMR (500 MHz, CDCl$_3$) δ 7.13-7.49 (m, 15H), 5.02-5.37 (m, 3H), 4.52-4.87 (m, 2H), 3.75-4.00 (m, 2H), 3.28-3.51 (m, 1H), 2.75-2.94 (m, 2H), 2.43 (s, 2H), 2.05 (s, 3H). $^{13}$CNMR (125 MHz, CDCl$_3$) 201.2, 168.4, 155.85, 140.91, 140.36, 138.22, 129.15, 128.68, 128.56, 128.37, 128.10, 127.72, 127.41, 127.64, 126.75, 80.23, 60.18, 54.14, 50.15, 7.99, 43.6, 37.43, 25.7.

Preparation of (2R,3S)-3-Cbz amino-2-hydroxy-4-phenyl-1-(N-benzyl-2-diazo-3-oxo-butanamido) butane (XII)

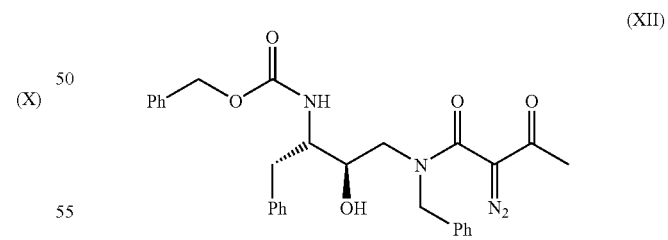

(XII)

The keto amide (XI) (0.040 g, 0.08 mmol) was dissolved in 0.5 ml of acetonitrile and cooled to 0° C. To this tosyl azide (0.024 g, 0.12 mmol) was added followed by the addition of DBU (18 μL, 0.12 mmol) dropwise. The reaction mixture was stirred for 1 hr at 0° C. and then 3 hrs at room temperature. It was then concentrated under reduced pressure to give dark red oil. The residue was taken up in a minimum volume of dichloromethane and placed on a silica gel column. The compound was eluted with 2:1 hexane/ethyl acetate to give the diazo keto-amide (XII) as yellow oil. 0.033 g (78% yield). $^1$H NMR (500 MHz, CDCl$_3$) δ 7.13-7.49 (m, 15H), 5.02-5.37 (m, 3H), 4.46-4.87 (m, 2H), 3.75-4.06 (m, 2H), 3.28-3.51 (m, 1H), 2.75-2.94 (m, 2H), 2.05 (s, 3H). $^{13}$CNMR (125 MHz, CDCl$_3$) 171, 165.4, 155.85, 140.91, 140.36, 139.22, 129.14, 128.68, 128.26, 128.17, 128.10, 127.72, 127.41, 127.64, 126.75, 79.23, 60.38, 53.14, 50.15, 47.99, 45.6, 37.43, 26.6.

Preparation of (2R,3S)-3-Cbz amino-2-hydroxy-4-phenyl-1-(N-benzyl-2-diazo-ethanamido) butane (BW1003) (XIII)

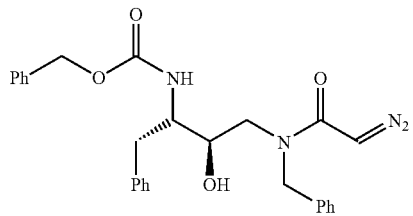

(XIII)

The diazo ketamide (XII) (0.020 g, 0.038 mmol) was dissolved in 0.5 ml of 1:1 THF/H$_2$O and to this LiOH (5 mg, 0.19 mmol) dissolved in 0.2 ml of water was added. The reaction mixture was stirred for 5 hrs and diluted with 2 ml of dichloromethane. The organic layer was separated, dried (Na$_2$SO$_4$), and concentrated. The product (XIII) was then isolated by passing through a plug of silica as an oil. 0.015 g. (81% yield). $^1$H NMR (500 MHz, CDCl$_3$) δ 7.13-7.49 (m, 15H), 5.02-5.37 (m, 3H), 4.46-4.87 (m, 2H), 3.75-4.04 (m, 2H), 3.28-3.47 (m, 1H), 2.75-2.94 (m, 2H). $^{13}$CNMR (125 MHz, CDCl$_3$) 163.4, 155.85, 140.91, 140.36, 139.22, 129.14, 128.68, 128.26, 128.17, 128.10, 127.72, 127.41, 127.64, 126.75, 78.33, 60.18, 52.04, 50.15, 46.89, 44.7, 36.43.

Preparation of (2R,3S)-3-azido-2-tetrahydrapyranyl-4-phenyl-1-naphthylmethyl amino butane (XIV)

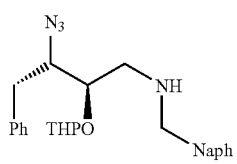

(XIV)

To a solution of tosyl protected alcohol (0.215 g, 0.48 mmol) in anhydrous THF (4 ml) naphthyl methyl amine (0.42 ml, 2.88 mmol) was added. The reaction mixture was refluxed at 90° C. for 56 hrs, cooled and then concentrated. Chromatography on silica gel with 1:1 hexane/ethyl acetate as eluent gave the product (XIV) as two isomers. 0.145 g (70% yield.) $^1$H NMR (500 MHz, CDCl$_3$) δ 7.80-8.07 (m, 4H), 7.15-7.31 (m, 20H), 4.66-4.78 (m, 2H), 3.78-4.21 (m, 10H), 3.48-3.58 (m, 2H), 2.84-3.12 (m, 6H), 2.66-2.79 (m, 2H), 1.45-1.98 (m, 12 H). $^{13}$CNMR (125 MHz, CDCl$_3$) 139.21, 139.01, 138.23, 138.08, 135.91, 135.86, 133.88, 133.67, 129.20, 129.15, 128.62, 128.56, 128.45, 128.37, 128.13, 128.09, 127.02, 126.88, 126.75, 126.66, 125.59, 125.46, 123.92, 123.84, 100.28, 99.15, 80.23, 78.84, 66.04, 65.12, 63.91, 63.19, 54.09, 53.98, 50.15, 47.99, 37.45, 36.35, 31.08, 31.06, 25.33, 25.24, 20.43, 19.81.

Preparation of (2R,3S)-3-amino-2-tetrahydrapyranyl-4-phenyl-1-naphthylmethyl amino butane (XV)

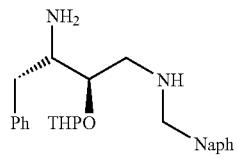

(XV)

The THP protected naphthyl methyl amine (XIV) (0.100 g, 0.233 mmol) was dissolved in 2 ml of absolute methanol in a 10 ml flask. The flask was degassed and the contents were cannulated to another 10 ml degassed flask containing 10% Pd/C in 1 ml of absolute methanol. The reaction mixture was then stirred in a hydrogen atmosphere for 12 hrs and then filtered through celite. The solvent was removed under reduced pressure and the residue was purified by silca gel chromatography with 5% methanol in chloroform as eluent to give the reduced amine (XV) as an oil and a mixture of isomers. 0.072 g (76%) yield. $^1$H NMR (500 MHz, CDCl$_3$) δ 7.81-8.07 (m, 4H), 7.05-7.31 (m, 20H), 4.64-4.76 (m, 2H), 3.78-4.18 (m, 10H) 3.32-3.58 (m, 4H), 2.84-3.12 (m, 4H), 2.66-2.78 (m, 2H), 1.42-1.57 (m, 12H).
$^{13}$CNMR (125 MHz, CDCl$_3$) 139.21, 139.01, 138.23, 138.08, 135.91, 135.86, 133.88, 133.67, 129.20, 129.15, 128.62, 128.56, 128.45, 128.37, 128.13, 128.09, 127.02, 126.88, 126.75, 126.66, 125.59, 125.46, 123.92, 123.84, 100.28, 99.15, 80.23, 78.84, 66.04, 65.12, 60.18, 60.09, 54.09, 53.98, 50.15, 47.99, 37.43, 36.35, 31.08, 31.06, 25.33, 25.24, 20.41, 19.81.

Preparation of (2R,3S)-3-Cbz amino-2-tetrahydrapyranyl-4-phenyl-1-naphthylmethyl amino butane (XVI)

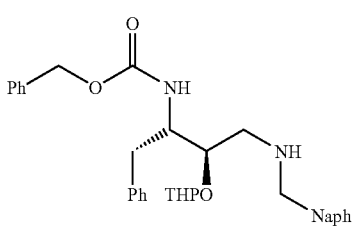

(XVI)

The reduced primary amine (XV) (0.072 g, 0.167 mmol) was taken up in 2 ml of ether along with 1 ml of saturated sodium bicarbonate solution and cooled to 0° C. Then benzyl chloroformate (34 μL, 0.23 mmol) was added dropwise to the reaction mixture and stirred for 5 hours. The aqueous layer was then separated, dried (Na$_2$SO$_4$) and the organic layer was concentrated under reduced pressure. It was then subjected to silica gel chromatography using 2:1 hexane/ethyl acetate as an eluent to give Cbz protected amine (XVI) as an oil and as mixture of isomers. 0.075 g (83%) yield. $^1$H NMR (500 MHz, CDCl$_3$) δ7.80-8.06 (m, 4H), 7.08-7.48 (m, 30H), 5.01-5.33 (m, 6H), 4.68-4.84 (m, 2H), 3.74-4.14 (m, 8H), 3.36-3.62 (m, 4H), 2.82-3.10 (m, 4H), 2.66-2.78 (m, 2H), 1.42-1.93 (m, 12H). $^{13}$CNMR (125 MHz, CDCl$_3$) 155.87, 155.78, 140.91, 140.84, 140.42, 140.30, 138.22, 138.08, 135.91, 135.86, 133.88, 133.67, 129.20, 129.15, 128.74, 128.68, 128.61, 128.56, 128.44, 128.37, 128.13, 128.09, 127.02, 126.88, 127.72, 127.64, 127.43, 127.38, 126.75, 126.66, 125.59, 125.46, 123.92, 123.84, 100.28, 99.15, 80.23, 78.84, 71.88, 68.59, 66.04, 65.12, 60.18, 60.09, 54.09, 53.98, 50.15, 47.99, 37.43, 36.35, 31.08, 31.06, 25.33, 25.24, 20.41, 19.81.

Preparation of (2R,3S)-3-Cbz amino-2-hydroxy-4-phenyl-1-naphthylmethyl amino butane (XVII)

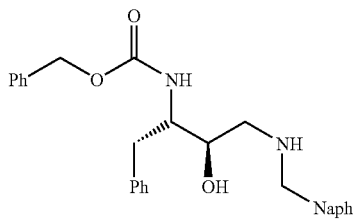

(XVII)

The Cbz protected amine (XVI) (0.075 g, 0.14 mmol) was dissolved in 2 ml of ethanol and to this 10 mol % of PPTS added. The reaction mixture was stirred at 60° C. for 5 hrs and it was then washed with saturated sodium bicarbonate solution. The organic layer was separated, dried (Na$_2$SO$_4$), and concentrated under reduced pressure. It was then subjected to silica gel chromatography with 2:1 hexane/EtAc as eluent to give the Cbz protected amino alcohol (XVII) as an oil. 0.060 g (94%) yield. $^1$H NMR (500 MHz, CDCl$_3$) δ 7.78-8.06 (m, 2H), 7.07-7.53 (m, 15H), 5.02-5.35 (m, 3H), 4.52-4.87 (m, 2H), 3.75-4.04 (m, 2H), 3.28-3.49 (m, 1H), 2.75-2.94 (m, 2H). $^{13}$CNMR (125 MHz, CDCl$_3$) 157.85, 139.91, 139.36, 138.22, 135.91, 125.39, 123.92, 129.15, 128.68, 128.56, 128.37, 128.10, 127.72, 127.41, 127.64, 126.75, 80.23, 60.18, 54.14, 50.15, 47.99, 37.43.

Preparation of (2R,3S)-3-Cbz amino-2-hydroxy-4-phenyl-1-(N-naphthylmethyl ethanamido) butane (BW1004) (XVIII)

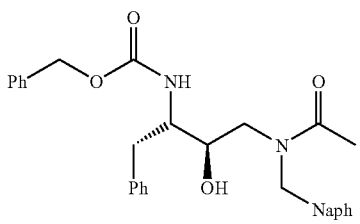

(XVIII)

The Cbz protected amino alcohol (XVII) (0.035 g, 0.076 mmol) was dissolved in 1 ml of anhydrous THF. To this triethylamine (0.11 mmol) was added dropwise. After 10 minutes acetic anhydride (0.11 mmol) was added and 1 mg of DMAP was added. The reaction mixture was stirred for 12 hrs and it was then washed with water. The organic layer was separated, dried (Na$_2$SO$_4$), and concentrated under reduced pressure. It was then subjected to silca gel chromatography with 2:1 hexane/ethyl acetate as eluent to give the acetylated amino alcohol (XVIII) as an oil. 0.028 g (73%). $^1$H NMR (500 MHz, CDCl$_3$) δ 7.80-8.06 (m, 2H), 7.13-7.49 (m, 15H), 5.02-5.37 (m, 3H), 4.52-4.87 (m, 2H), 3.75-4.00 (m, 2H), 3.28-3.51 (m, 1H), 2.75-2.94 (m, 2H), 2.07 (s, 3H). $^{13}$CNMR (125 MHz, CDCl$_3$) 168.4, 155.85, 139.41, 139.36, 138.22, 135.43, 129.15, 128.68, 128.56, 128.37, 128.10, 127.72, 127.41, 127.64, 126.75, 125.62, 123.75, 80.23, 60.18, 54.14, 50.15, 47.99, 37.43, 17.1.

Reference is made herein to specific embodiments. Each embodiment is provided by way of explanation of the invention, not as limitation of the invention. In fact, it will be apparent to those skilled in the art that various modifications and variations can be made in the present invention without departing from the scope or spirit of the invention. For instance, features illustrated or described as part of one embodiment may be incorporated into another embodiment to yield a further embodiment. Thus, it is intended that the present invention cover such modifications and variations as come within the scope of the appended claims and their equivalents.

Although specific embodiments of the various compounds and methods have been described, the present invention should not be construed so as to be limited to just those embodiments. It should be understood that the above examples are given only for the sake of showing that the compounds and methods can be made. The above devices and methods can be generalized to encompass a broad genus. In this vein, any one or more features from any of the disclosed embodiments above can be combined with any one or more features from any other embodiment. Accordingly, the above written description is not meant to limit the invention in any way. Rather, the below claims define the invention.

What is claimed is:
1. A compound of formula (I):

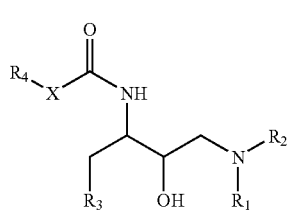

(I)

wherein R$_1$ and R$_2$ independently are halogen; hydroxyl; alkoxy; acyl; cyano; nitro; amino; substituted or unsubstituted alkyl, alkenyl, or alkynyl groups; or substituted or unsubstituted aromatic or cyclic aliphatic groups, which may include one or more heteroatoms in the ring;

wherein, R$_3$ and R$_4$ independently are hydrogen; halogen; hydroxyl; alkoxy; acyl; cyano; nitro; amino; substituted or unsubstituted alkyl, alkenyl, or alkynyl groups; or substituted or unsubstituted aromatic or cyclic aliphatic groups which may include one or more heteroatoms in the ring;

wherein substituted means substituted with one or more identical or different substituents selected from the group consisting of halogen, hydroxyl, alkyl, alkenyl, alkynyl, alkoxy, cycloalkoxy, haloalkyl, haloalkoxy, acyl, amino, alkylamino, dialkylamino, nitro, cyano, thio, alkyl thio, alkenylthio, alkynylthio, sulfonyl, alkylsulfonyl, sulfinyl, and alkylsulfinyl; and wherein X is a heteroatom selected from O, N, or S.

2. The compound of claim 1, wherein wherein $R_1$ and $R_2$ are independently acyl or substituted or unsubstituted aromatic, heteroaromatic, cyclic aliphatic, or heterocyclic aliphatic rings, and $R_3$ and $R_4$ are independently hydrogen; acyl; or substituted or unsubstituted aromatic, heteroaromatic, cyclic aliphatic, or heterocyclic aliphatic rings.

3. The compound of claim 1, wherein $R_1$, $R_3$, and $R_4$ independently are substituted or unsubstituted phenyl, benzyl, or napthylmethyl; and wherein $R_2$ is selected from the group consisting of acetyl, diazoacetyl, and benzoyl groups.

4. The compound of claim 1, wherein the compound is a diastereomerically pure compound wherein the stereocenters have the configuration RR, RS, SR, or SS.

5. The compound of claim 1, wherein the compound is in a formulation comprising the compound and a pharmaceutically acceptable carrier.

6. The compound of claim 1, wherein the compound enhances lysosomal function.

7. The compound of claim 1, wherein the compound activates one or more lysosomal enzymes.

8. The compound of claim 1, wherein the compound reduces the accumulation of abnormal proteins when administered to an animal.

9. The compound of claim 8, wherein the abnormal protein is abnormal amyloid precursor protein, abnormal alpha synuclein protein or abnormal huntingtin protein.

10. A method for the treatment of a neurodegenerative disorder comprising administering to a human in need thereof an effective amount of a compound of claim 1, wherein the neurodegenerative disorder is selected from the group consisting of Alzheimer's Disease, Parkinson's Disease, Huntington's Disease, and amyotrophic lateral sclerosis.

* * * * *